United States Patent [19]

McDonald

[11] 4,100,023
[45] Jul. 11, 1978

[54] DIGESTER AND PROCESS FOR CONVERTING ORGANIC MATTER TO METHANE AND FERTILIZER

[76] Inventor: Byron A. McDonald, R.D. 2, Baraboo, Wis. 53913

[21] Appl. No.: 785,777

[22] Filed: Apr. 8, 1977

[51] Int. Cl.² .............................................. C12D 3/10
[52] U.S. Cl. ..................................... 195/27; 195/141; 195/142; 195/143; 195/144; 48/197 A; 71/9; 71/10
[58] Field of Search ............... 195/141, 142, 144, 143, 195/27; 48/197 A; 71/9, 10

[56] References Cited

U.S. PATENT DOCUMENTS

| 1,919,689 | 7/1933 | Elrod | 48/197 A |
| 2,123,463 | 7/1938 | Effront | 195/142 |
| 2,847,352 | 8/1958 | Delacommune | 195/144 |
| 3,405,920 | 10/1968 | Lefrancois | 195/143 |
| 3,981,803 | 9/1976 | Coulthard | 48/197 A |
| 4,022,665 | 5/1977 | Ghosh et al. | 195/144 |

*Primary Examiner*—Alvin E. Tanenholtz
*Attorney, Agent, or Firm*—John T. Matlago

[57] ABSTRACT

A digester is disclosed for controlling the decomposition of organic matter to produce a useful gas and a liquid fertilizer. The digester comprises three slurry chambers connected in tandem by passthrough tubes. A fourth chamber used for gas collection is located above the three slurry chambers. An input line is connected to the bottom of the first chamber and an output line is connected to the bottom of an upright tube provided in the third chamber. A slurry containing raw manure or other organic waste is loaded from a mix tank through the input line to fill the three chambers to a level determined by the top of the upright tube in the third chamber. The process of aerobic digestion and a limited form of anaerobic digestion is carried out in the first chamber and the process of anaerobic digestion which produces the methane gas is carried out in the second chamber which is heated. As an input load of slurry is fed daily from the mix tank into the first chamber, the digested slurry in the third chamber in addition to being fed out through the upright tube as a liquid fertilizer has a small portion thereof recycled back into the mix tank to condition the input load. The gas collected in the fourth chamber is compressed and stored. Such gas in addition to being available for general usage provides for heating the water used to heat the second chamber and for agitating the slurry in the three slurry chambers.

11 Claims, 7 Drawing Figures

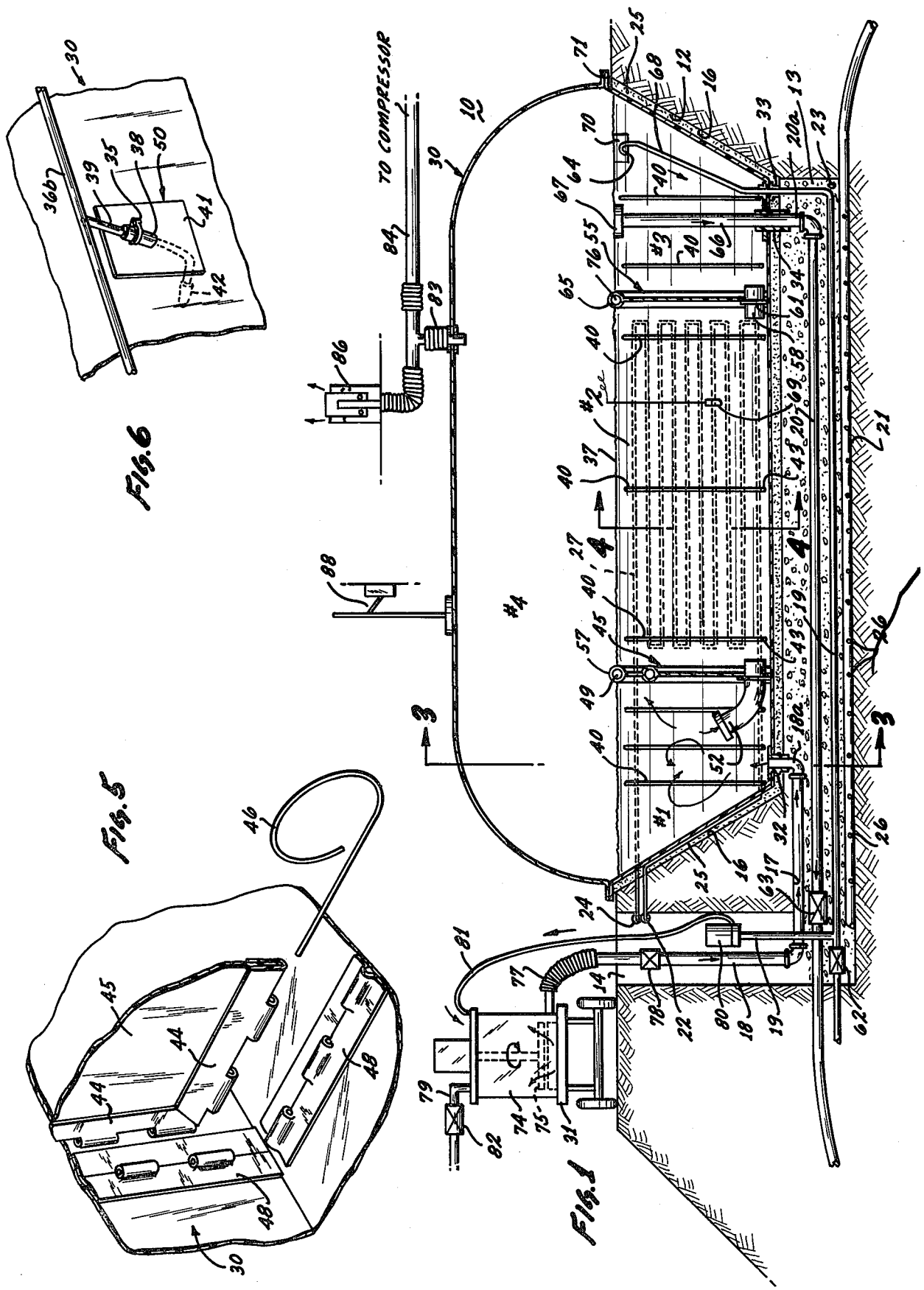

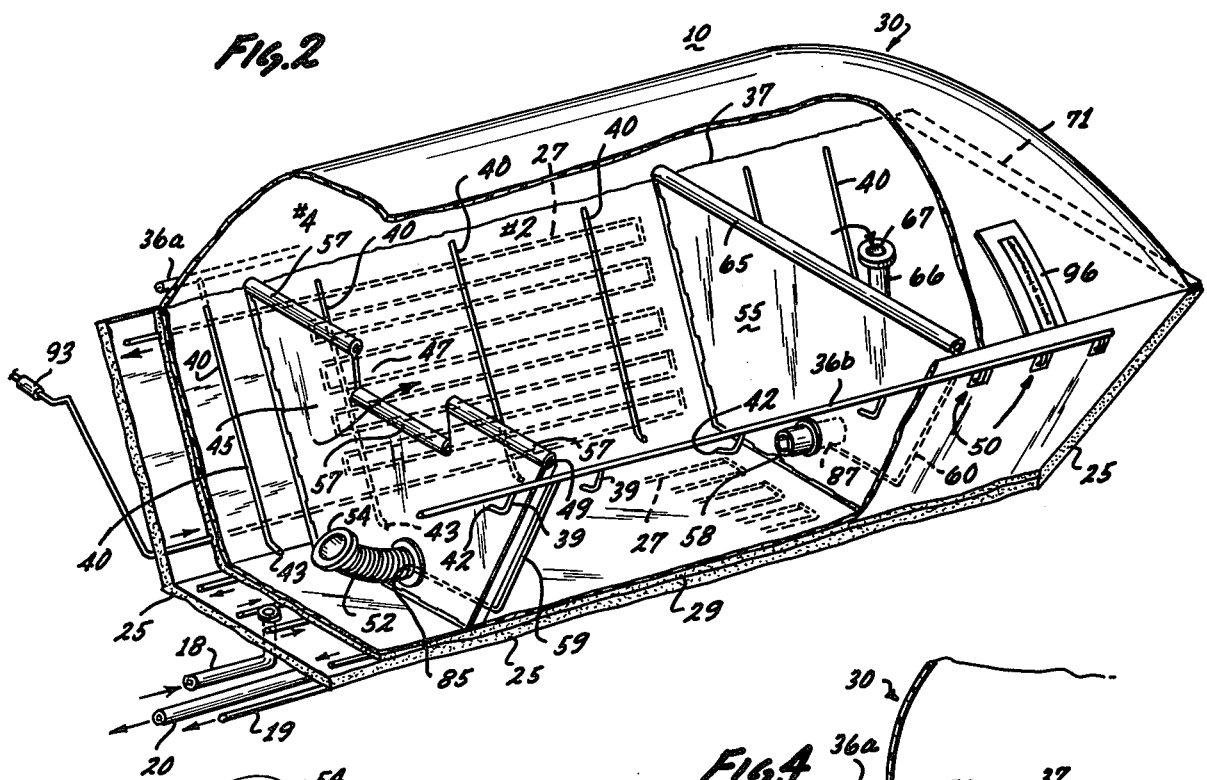
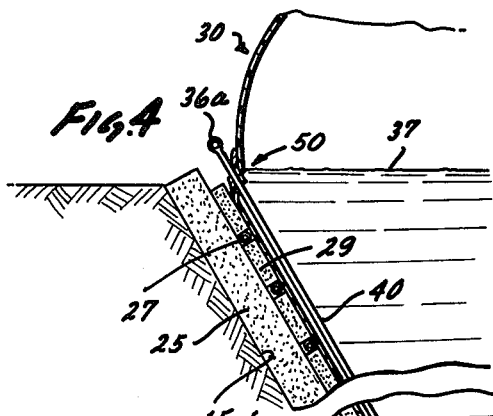
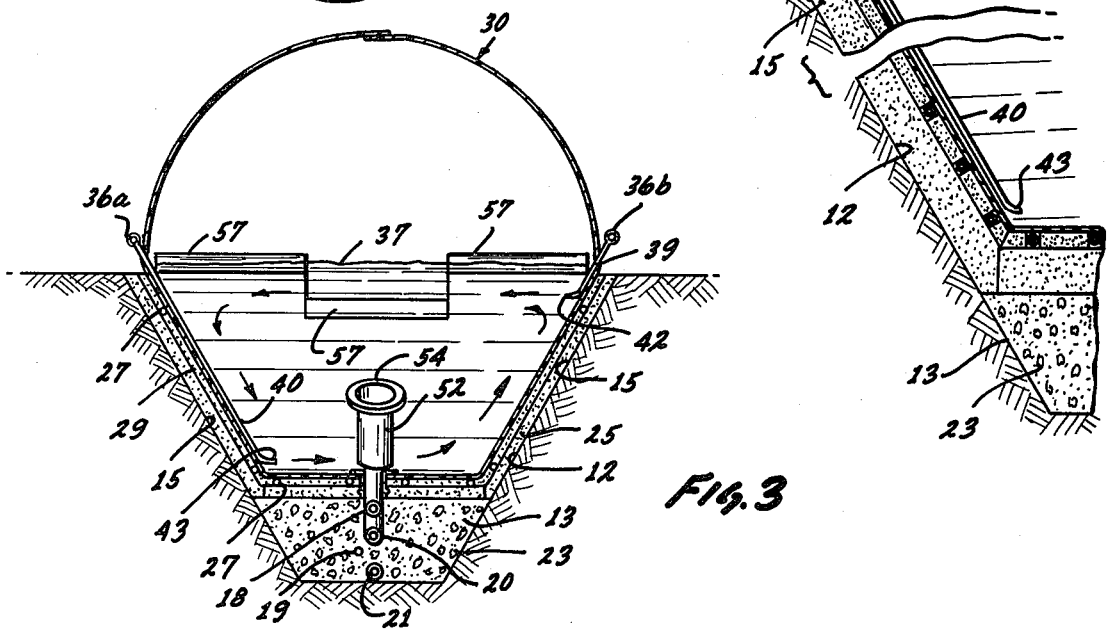

DIGESTER AND PROCESS FOR CONVERTING ORGANIC MATTER TO METHANE AND FERTILIZER

BACKGROUND AND SUMMARY OF THE INVENTION

This invention relates to apparatus for the anaerobic digestion of organic matter and more particularly to a digester for controlling the process of the decomposition of organic matter to produce a useful gas and a liquid fertilizer.

The theory of anaerobic digestion and its application to produce methane are well known. Thus, many municipal sewage processing systems incorporate an anaerobic stage and use the gas produced during this time as a fuel for providing heat and operating stationary engines. The primary purpose of such systems, however, is not to produce the useful gas but rather to rapidly decontaminate and liquify the organic waste before dumping it into streams and landfills.

Such systems are impractical for farm usage where it is desired to efficiently produce a useful gas (approximately 70% methane and 30% carbon dioxide) and a high quality liquid fertilizer from manure and other forms of organic waste that have in the past either been wasted or have not been fully exploited.

In accordance with the present invention it is recognized that in the process of organic decay, i.e., digestion of organic waste, which results in the production of methane gas, different kinds of bacteria have to grow and do their work in sequence. First, various types of aerobic bacteria, i.e., bacteria that require oxygen, must form in the organic waste to convert oxygen from its free state into carbon dioxide and to otherwise decompose the material. Then, various types of anaerobic bacteria, i.e., bacteria that live in the absence of oxygen, must form and feed off the oxygen-freed, but still raw organic waste. As these bacteria become active, the products of the first provide food for the next until a food acceptable to the methane producing anaerobic bacteria is reached. Until the stage of methane production is reached the bacteria are relatively insensitive to changes in temperature. But, methane producing bacteria are very sensitive and must have favorable conditions in order to grow and multiply.

The digester of the present invention takes into account the activity and characteristics of the microbial action which takes place during the course of complete anaerobic digestion. Thus the digester is constructed to accommodate the natural behavior of the several forms of bacteria by providing three slurry chambers in tandem, each separated from the other by a passthrough tube, and a fourth chamber, located above the three slurry chambers, which serves to collect the gas produced. Of the three slurry chambers, only the second chamber is heated. Thus the non-heated first or input chamber receives the input load of the new waste material such as raw manure which is fed from a mix tank to the digester daily. This first chamber accomodates and separates the activity of the temperature insensitive bacteria and at the same time serves to insulate the second or incubation chamber which is heated to ac-, comodate the temperature sensitive bacteria which produces methane. At the same time, advantage is taken of the heat lost from the heated second or incubation chamber to warm and thus stimulate digestion in the first chamber. This same warming is extended to the nonheated third or temporary storage chamber where biological activity slows down, yet some gas production is stimulated by heat. Then to further increase the efficiency of the operation, a required amount of digested manure which collects in the third chamber is recycled back to the mix tank. This not only serves to liquify and warm the new raw manure before it is fed into the first chamber, but, being saturated with bacteria, the digestive process begins immediately.

Accordingly, one of the subjects of the present invention is to provide an anaerobic digester that is practical for use on the farm or other animal raising areas for producing a fuel-type gas from organic waste materials.

Another object of the present invention is to provide a digester having separate chambers for accomodating the natural behavior of the several forms of bacterial action that take place in the course of the decomposition of raw organic matter to produce a useful gas and a liquid fertilizer.

Still another object of the present invention is to provide a cost-effective system for operating on organic waste matter to form a useful gas and a high quality liquid fertilizer.

Yet another object of the present invention is to provide an efficient anaerobic digester that is simply constructed, and easy to install and maintain on a farm.

With these and other objects and advantages in view, the invention consists of the construction, arrangement and combination of the various parts of the device, whereby the objects contemplated are obtained as hereinafter set forth, pointed out in the appended claims and illustrated in the accompanying drawings.

BRIEF DESCRIPTION OF THE DRAWINGS

FIG. 1 shows a sectional side view of the digester of the present invention together with a diagrammatic illustration of associated equipment;

FIG. 2 is a perspective view of the digester with portions thereof cutaway to show the interior structure thereof;

FIG. 3 is a cross sectional view of the digester as taken along line 3—3 of FIG. 1;

FIG. 4 is a cross sectional view of one side of the digester as taken along line 4—4 of FIG. 1;

FIG. 5 is a detail showing of the hinged connection of a divider to the sidewall of the digester;

FIG. 6 is a perspective view of a shroud coupling for a gas jet connector; and

FIG. 7 is a perspective view showing the structure of the passthrough tube for the first divider.

DESCRIPTION OF THE PREFERRED EMBODIMENT

Referring to the drawings, the digester 10 of the present invention includes a trench 12 which is dug into the ground preferably on a higher level of the terrain. The trench 12 has a bottom portion 13 with outwardly slanting flat sides 15 extending up to ground level and with outwardly slanting flat ends 16 extending up from the top of the bottom portion 13 to ground level. A vertical access hole 14 is dug into the ground spaced from the front end of the trench 12 and a tunnel 17 is provided for connecting the bottom portion 13 of the trench 12 with the bottom of the access hole 14.

An input line 18 extends down into the access hole 14 and through the tunnel 17 and has an upturned end 18a located near the front of the bottom portion 13 of the trench. A digest recycle line 19 has an upturned end 19a located near the back of the bottom portion 13 of the trench and extends therefrom through the tunnel 17 and up into the access hole 14. An output line 20 which has an upturned end 20a also located near the back of the bottom portion 13 of the trench 12 extends therefrom through the tunnel 17 and on through the ground to a field or spreader (not shown) located at a lower level of the terrain. Also located in the bottom portion 13 of the trench 12 and extending along the length thereof is a drainage pipe 21 having spaced holes 26 in its walls. The drainage pipe 21 preferably slopes slightly downwardly toward the rear of the trench such as to drain any fluid which might collect in the bottom portion 13 of the trench to a lower level of the terrain.

The bottom portion 13 of the trench 12 is filled with gravel 23 which surrounds the lines 18, 19, 20 and the pipe 21 and provides a substantially level upper surface through which the upturned ends 18a, 19a and 20a of the lines extend.

A layer 25 of foam insulation is laid down so as to cover the sides 15, the ends 16, and the surface of the gravel 23 on the bottom portion 13 of the trench with the upturned ends 18a, 19a and 20a of the respective lines 18, 19 and 20 extending therethrough. The thickness of layer 25 is a function of the temperature variations of the climate in the area in which the digester is being installed.

Tubing shaped to form longitudinally extending heating coils 27 is laid down on the layer 25 of insulation in the central portions of the sides and the gravel bottom of the trench 12. Provided on the front end of the trench is an inlet pipe 22 and an outlet pipe 24 for supplying hot water into and out of the heating coils 27 located on one side of the trench. Similar inlet and outlet pipes (not shown) are provided for the heating coils 27 located on the other side and the bottom of the trench. A second layer 29 of foam insulation is then placed over the layer 25 between the coils of tubing 27 and throughout the remainder of the sides and the bottom of the trench 12. The purpose of the insulation is to enable the digester to operate effectively in cold climate.

Placed in the trench 12 so as to lie against the flat bottom and side surfaces provided by the top layers 29 of insulation is a digester bag 30 made of a commercially available reinforced elastomeric structural fabric. Such a fabric is tough and fluid tight, is unaffected by sun radiation and other environmental factors, and has a long life. The bag 30 which is in the shape of a pillow or oblong balloon when inflated, lies on its side with its bottom half portion supported by the layer 29 of insulation placed on the gravel bottom and sides 15 and ends 16 of the trench. The bottom of the bag 30 is provided with openings at appropriate locations which have flanged shroud connectors 32, 33 and 34 secured thereto for receiving the respective upturned ends 18a, 19a and 20a of the input line 18, the digest recycle line 19, and the output line 20. These flanged shroud connectors are preferably molded of the aforementioned elastomeric structural fabric.

The lower portion of the bag 30 which is supported within the trench 12 is separated by a first divider 45 and a spaced second divider 55 to form three successive chambers #1, #2 and #3. The dividers 45 and 55 may be made of the same structural fabric used for the bag. The divider 45 is cut to have a shape corresponding to the cross section of the trench. A weir 47 is formed on the top of the divider 45. The sides and bottom of the divider 45 have bonded thereon, by use of an adhesive, piano hinge strips 44 which interfit with mating piano hinge strips 48 secured to the sides and bottom of the bag. The hinge strips 44 and 48 may be made of the same structural fabric used for the bag. A piano hinge pin 46 in the form of a plastic tubing is inserted in the mated aligned openings of piano hinge strips 44 and 48 to hold the divider 45 to the bag.

Rods of foam plastic 49 are fitted into cylindrical pockets 57 formed on the upper edges of the divider 45. An elbow shaped passthrough tube 52 having its free end opening upwardly is located in chamber #1 for enabling slurry in the central portion thereof to flow into chamber #2. As shown in FIG. 7, the passthrough tube 52, which is preferably formed of a slurry resistant fabric, is reinforced and shaped by stainless steel wiring 53. The passthrough tube 52 has a foam plastic float collar 54 on its upper free end and a flange 56 on its opposite end by which it is attached about an opening provided on the bottom of the divider 45. The purpose of passthrough tube 52 is to equalize the pressure between chambers #1 and #2 during initial loading and during the daily loading of the digester. However, the passthrough tube further operates to restrict the new input into chamber #1 from entering chamber #2 while allowing the partly digested slurry in the central portion of chamber #1 to flow into chamber #2.

The second divider 55 may likewise be formed of the same synthetic structural fabric used for the bag and similarly is held by a piano hinge pin 46 passing through openings on piano hinge strips 48 secured to the sides and bottom of the bag and mating hinge strips 44 secured to the sides and bottom edges of the divider 55. A rod of foam plastic 76 is fitted into a cylindrical pocket 65 formed on the upper edge of divider 55. A passthrough tube 58 for divider 55 in the form of a straight and rigid cylinder extends through an opening provided at the bottom center of the divider 55 and is attached by a flange 61 such as to protrude equally from either side thereof. The passthrough tube 58 is likewise formed of a slurry resistant fabric and reinforced with stainless steel wiring similar to the passthrough tube 52. The purpose of the passthrough tube 58 is to equalize the pressure between chambers #2 and #3 during initial loading and during the daily loading of the digester. The locating of passthrough tube 58 at the bottom of the divider 55 assures that the settled spent digest slurry in chamber #2 will flow into chamber #3.

Main gas tubes 36a and 36b are placed to extend horizontally along either side of the digester bag 30 at ground level. The sides of bag 30 just below the level of the slurry are provided with a plurality of spaced openings. A shroud coupling 50 is bonded about each of the openings. The shroud coupler 50 which is also preferably molded of the same structural fabric used for the bag includes a small flat piece 41 of this material having an angularly disposed tubular portion 38 in the center thereof which is aligned with the opening in the bag. A shroud coupler clamp 35 of stainless steel is provided on the tubular portion 38.

The main horizontal tube 36b on one side of the bag 30 has short connectors 39 branching off along the length thereof. Each short connector 39 passes through the tubular portion 38 of a shroud coupler 50 on the side of the bag 30 and is held by a coupler clamp 35. An upper jet 42 is attached to or formed on the end of each short connector 39. The main horizontal tube 36a on the other side of the digester bag 30 has long connectors 40 branching off along the length thereof. Each long connector 40 passes through the tubular portion 38 of a shroud coupler 50 secured on the other side of the bag and down into the bottom of the bag and is held by a coupler clamp 35. A lower jet 43 is attached to or formed on the end of each long connector 40.

It should be noted that the main gas tube 36b also has a branch connector 59 which extends through the side of the bag and down to the exit end of the passthrough tube 52 with a jet 85 on its end directed inwardly therein. Likewise, the main gas tube 36b has a branch connector 60 which extends through the side of the bag and down to the exit end of the passthrough tube 58 with a jet 87 on its end directed inwardly therein.

To fabricate the digester bag 30 as above described, a large flat rectangular sheet of elastomeric structural fabric may be laid out on a flat surface such as the ground. At appropriate locations on the portion of the sheet of fabric corresponding to the bottom of the bag, openings are cut and the flanged shroud connectors 32, 33 and 34 are bonded thereon for receiving the respective upturned ends 18a, 19a and 20a of the input line 18, the recycle line 19, and the output line 20. In addition, at appropriate locations on the portion of the sheet of fabric corresponding to the sides of the bag, openings are cut for the jet connectors 39 and 40 and the shroud couplings 50 such as shown in FIG. 6, are then bonded in position about each of these openings. Further, to permit access to the interior of the upper half of the bag one or more zipper assemblies 96 are bonded to corresponding portions of the sheet. The dividers 45 and 55 and the mating strips of piano hinges 44 and 48 are then cut from the same structural fabric. After the mating strips 48 and 44 of piano hinges are bonded to locations on the sheet connecting to the respective sides and bottom portions of the bag 30 and to the edges of the dividers 45 and 55, the dividers are then attached to the bag by use of the hinge pins 46. Preferably the passthrough tubes 52 and 58 are attached to the respective dividers 45 and 55 at this time. The opposite sides of the sheet of structural fabric are then folded upwardly and the edges thereof overlapped and joined using an adhesive solvent. The ends 71 of the cylindrical structure of fabric thus formed are then simply pinched together using the adhesive solvent.

When the digester bag 30 is fabricated and first laid in its supportive trench 12, the flanged shroud connectors 32, 33 and 34 are fitted on the upturned ends 18a, 19a and 20a of the respective lines 18, 19 and 20 and the external valves 62 and 63 on the output lines 20 and 19 are closed. In addition, the connectors 39 and 40 for the upper and lower jets 42 and 43 are inserted and clamped in the shroud couplers 34 provided on the side of the bag. A small amount of water is then allowed to flow through the inlet line 18 to shape the fabric of the bag 30 to the contour of the trench. The unsupported upper half of the bag 30 is then inflated with compressed air and checks are made for leakage. It should now be clear that the bottom half portion of the bag together with the supportive trench 12 provides the digest tank forming the three slurry chambers #1, #2 and #3 and the flexible top half portion of the bag provides the gas collector chamber #4.

By gaining access into the interior of bag 30 by use of the zipper assembly 96 provided on the upper side thereof, an upright pipe 66 is connected to the flanged shroud connector 34 on the upturned end 20a of the output line 20 on the bottom of the chamber #3. The upper end of this upright pipe 66 forms the outlet port 67 to the output line 20.

A flexible tubing 68 is also positioned in the chamber #3 with its bottom connected by way of the flanged shroud connector 33 to the upturned end 19a of the digest return line 19. This upper end 64 of tubing 68 forms the inlet port to the digest recycle line 19. The outlet port end 64 of tubing 68 is bent down and held by a float 70 such as to be located just below the surface, i.e., the fluid line 37, of the slurry in chamber #3 which level is determined by the outlet port 67 on the upright pipe 66.

Schematically shown as supported from the ground or a structure near the upper inflated half portion of the bag 30 is a gas outlet pipe 83. The outlet pipe 83 has one end thereof flexibly connected to an opening in the bag by a shroud coupling, similar to coupling 50, and its other end connected to a pipe 84 leading to a compressor (not shown). This outlet pipe 83 is provided with a pressure relief valve 86, schematically shown, set to open at 3 inches of water column pressure.

An on-off compressor control switch 88 may be provided which is supported from the ground or a structure near the inflated flexible upper half portion of the bag 30. This switch 88 senses when chamber #4 comprising the upper half portion of the bag 30 has expanded due to buildup of the gas generated in the digester 10 and operates to start the compressor to withdraw the gas. The switch 88 also senses the contraction of chamber #4 and operates to stop the compressor.

It should now be clearly understood that the three consecutive slurry chambers #1, #2 and #3 provide a continuous and efficient digester which accomodates the variety of bacterial action that takes place during digestion of waste materials. Chamber #1 is approximately the same size as chamber #3 while chamber #2 is approximately three to four times the size of chamber #1. As will be discussed further hereinafter, such a construction enables the slurry to be detained on the order of 3 to 4 days in chamber #1, 10 to 15 days in chamber #2, and 3 to 4 days in chamber #3. The spread in the detention time in the different chambers takes into account the volume of the input load introduced into the chamber #1 daily, which causes the movement of a like volume of the slurry from chamber #1 to chamber #2, from chamber #2 to chamber #3, and from chamber #3 into the output line 20.

Shown positioned on a conveyor 31 located at ground level adjacent the access hole 14, but which may be spaced away therefrom, is a mix tank 74 for receiving the raw manure or other organic waste to be used for the digester 10. Located adjacent to the top of the mix tank 74 is a pipe line 79 for supplying water. The tank 74 has a power driven blender-chopper 75 therein and has an output line connected to the bottom thereof including a flexible section 77 which connects by way of a control valve 78 to the upper end of the inlet line 18 leading to chamber #1 of the digester. The end of the digest recycle line 19 leading from chamber #3 is connected by way of a pump 80 to a flexible tube 81 leading up into the mix tank 74.

OPERATION

To operate the digester, the organic waste from a conveyance is placed in the mix tank 74 and the valve 83 in water line 79 is opened. Enough water is then added to the mix tank 74 to reduce the solids of the resulting slurry to a value of 8 to 10%. The blender 75 serves to chop up and finely grind the solids which may contain bedding, hay, silage and other bulky floatations.

By opening inlet valve 78, the new slurry as prepared in the mix tank 74 is fed by gravity through the input line 18 into the bottom of chamber #1, resulting in the slurry in chamber #1 flowing through the passthrough tube 52 into chamber #2, and the slurry in chamber #2 flowing through the passthrough tube 58 into chamber #3. Preferably at startup of the digester, enough slurry is initially introduced in this way to fill all three chambers #1, #2 and #3 to a fluid level 37 as determined by the location of the outlet port 67 on the upper end of the upright pipe 66 in chamber #3.

It should be noted that at start-up of the digester, valve 93 is opened to permit hot water to be introduced into the water inlet pipe 22. This water circulates in the heating coils 27 to heat the environmentally sensitive chamber #2 to a temperature of approximately 95° F. as indicated by a temperature sensor 69.

It should now be clear that with all three of the chambers loaded, each time a predetermined volume of shock load from the mix tank 74 is fed into chamber #1, an equal volume of slurry is caused to flow from chamber #1 through the weir 47 and passthrough tube 52 to chamber #2, and from chamber #2 through passthrough tube 58 into chamber #3. The overflow of the slurry in chamber #3 into the outlet port 67 of the upright pipe 66 causes an equal volume of the slurry to flow from the digester into the output line 20.

The volume of the chamber #1 is large enough to detain the daily input fed therein long enough for the slurry material to be prepared for the action taking place in the incubation chamber #2. Thus the slurry material in chamber #1 provides food for the relatively temperature insensitive aerobic bacteria whose digestive action removes free oxygen from the input slurry to form carbon dioxide. This aerobic bacteria, by digestive action, provides a food substance for the relatively temperature insensitive anaerobic bacteria which, in turn, by digestion produces an acetate and hydrogen on which the anaerobic and temperature sensitive methane producing bacteria will thrive in chamber #2. In addition, the bacterial action in chamber #1 results in acidified material rising in chamber #1. This acidified material is food needed for methane producing bacteria.

The volume of chamber #2 is sufficient to detain the slurry material therein long enough to efficiently extract methane therefrom. Thus the slurry which has been introduced into chamber #2 from chamber #1 initiates digestive action by the methane producing bacteria which results in methane being generated and collected in the flexible chamber #4. As a result of the action by the methane producing bacteria the slurry material tends to settle in chamber #2.

The slurry in chamber #3 provides for some final gas production but the biological activity therein slows down. Chamber #3 also serves as an insulation for the environmentally sensitive chamber #2, as the interface for liquid fertilizer drawoff into output line 20, and as a reservoir for recycling the digest to condition the input. Thus, to further increase the efficiency of operation the digest slurry in chamber #3 is recycled back into the mix tank 74 by flowing through the flexible line 68 and through the digest recycle line 19 and being pumped by pump 80 into mix tank 74. This not only serves to liquify and warm the new raw material in the mix tank before it is fed to chamber #1 but being activated with bacteria the digestive process begins immediately, i.e., bacteria is ready to go to work on the new manure.

It should now be clear that as a result of the daily shock load of raw waste being introduced from the mix tank 74 into chamber #1, the concentration of acidified material in chamber #1 which has risen toward the upperhalf of chamber #1 is caused to be moved through weir 47 in the divider 45 into chamber #2. In addition, some acidized material in chamber #1 is caused to be moved down into the mouth of the passthrough tube 52 on the bottom of divider 45 into chamber #2. Simultaneously, the heavily concentrated spent material which has settled in chamber #2 and is the product of anaerobic digestion is caused to flow through the passthrough tube 58 located in the bottom of divider 55 into chamber #3. The slurry which enters into chamber #3 is a high quality fertilizer.

Bulky floatations of the size found near the surface in chambers #1 and #2 are undigested matter. If this bulky floatation is allowed to enter chamber #3 it may pass into the recycle line 18 and the outlet line 19, leading to inefficiency of output production and clogging of the pump and valves. Accordingly, only digested slurry which has humus uniformly dispersed therethrough should be transferred into chamber #3.

It should be appreciated that the volume of the daily load entered into chamber #1 from the mix tank 74 is approximately one third to one fourth the volume of the chamber #1. Thus, based on an approximate last in-last out basis this slurry material fed into chamber #1 will tend to be detained therein approximately three to four days. On the other hand, the volume of the new material fed daily into chamber #2 from chamber #1 is approximately one tenth to one fifteenth the volume of chamber #2. Thus, based on an approximate last in-last out basis the slurry material fed into chamber #2 will tend to be detained therein approximately 10 to 15 days. Likewise, the volume of new material fed daily into chamber #3 from chamber #2 is approximately one third to one fourth the volume of chamber #3. Thus, based on an approximate last in-last out basis the slurry material fed into the chamber #3 will tend to be detained therein approximately 3 to 4 days.

In order to aid in the digestive process as above described, the slurry is agitated in each of the three chambers #1, #2 and #3 by use of the upper and lower gas jets 42 and 43. Gas for this purpose is drawn from pressurized tanks containing gas taken from chamber #4. Therefore, a small amount of gas which is compatible with digestion is efficiently recycled to provide a necessary amount of agitation. It should now be noted that this agitation must not take place for a certain period prior to the feeding of the daily load into chamber #1 which causes an equal volume movement from each chamber to the succeeding chamber and on out the output line 19. The reason for this is that the action of the bacteria on the materials in chamber #1 causes the reacted material to locate itself in the chamber #1 such that it tends to move and flow through the weir 47 and the passthrough tube 52 into chamber #1. Likewise, the action of the bacteria on the materials in the chamber #2, causes the material to be spent and settle toward the bottom of the chamber such that it tends to move and flow through the passthrough tube 58 into chamber #2.

When the undigested slurry is introduced into the chamber #1, it will tend to separate and cake therein. To avoid this, the upper gas jets 42 located along the top of one side and the lower gas jets 43 located along the bottom of the other side of the chamber #1 are spaced and adjusted so as to violently force a circulation of the slurry material throughout chamber #1, as illustrated in FIG. 3. This agitation may be manually or automatically regulated several times each day for short periods of time, but, as previously pointed out, not during the period just prior to the inputting of new slurry material, thus insuring the inducement of acidic material into chamber #2. Note that the gas jet 85 located at the base of the passthrough tube 52 operates to assure that the slurry does not cake in the passing therethrough.

In chamber #2, agitation is similarly provided by upper and lower gas jets 42 and 43. However, the gas jets are spaced further apart in chamber #2 and they are adjusted so that the circulation is less violent than in chamber #1. Here the purpose of the upper and lower jets 42 and 43 is to move the food substance, thus stimulating the anaerobic digestion and the production of methane. Note that the gase jet 87 located at the base of the passthrough tube 58 operates to assure that the slurry does not cake in passing therethrough.

In chamber #3, the digest will be as thin as water and homogeneous. Nevertheless with time, settlement and floatation of the humus can occur if agitation is not provided. Accordingly, the gas jets 42 and 43 are spaced apart and adjusted as in chamber #2 since only enough agitation is needed therein to ensure against separation.

The top flexible half of the digester bag 30 which serves as the gas collector chamber #4 expands or contracts (always at a pressure above atmosphere) with a slight amount of pressure change. Thus, the compressor control switch 88 which senses this expansion and contraction of the flexible bag 30 starts and stops the compressor which draws the gas in chamber #4 through pipe 84 into high pressure storage tanks. Accordingly, gas is automatically transferred from chamber #4 while maintaining a gas bag pressure between 1 and 3 inches water column. This pressure range assures a hard enough bag to withstand forces of the environment. Should the compressor control switch 88 fail the pressure relief valve 86 is provided in pipe 84 which may be simply an open ended manometer with a fluid level set for 3 inches water column maximum.

While the description has been concerned with a particular illustrative embodiment of the present invention, it will be appreciated that many modifications and variations in the construction and arrangement thereof may be provided for without departing from the spirit and scope of the invention or sacrificing any of its advantages and the invention is therefore to be limited only as indicated by the scope of the appended claims.

What is claimed is:

1. A digester for controlling the decomposition of organic matter to produce methane gas and a liquid fertilizer comprising:
   first, second and third slurry chambers disposed in tandem;
   a flexible chamber located above and covering said slurry chambers;
   a first passthrough tube connecting said first chamber to said second chamber and disposed to pass slurry from the central level portion of said first chamber to the lower level portion of said second chamber;
   a second passthrough tube connecting said second chamber to said third chamber and disposed to pass slurry from the lower level portion of said second chamber to the lower level portion of said third chamber;
   an input line connected for periodically feeding a load of raw slurry into the bottom of said first chamber; and
   an output line connected to the bottom of an upright pipe in said third chamber, the upper end of said upright pipe being the outlet port into which the slurry in the third chamber drains for feeding into the output line;
   whereby the periodical feeding of a load of raw slurry into said first chamber results in an equal volume of slurry being automatically transferred from each chamber to the next and into the output line; and
   wherein the size of the said first chamber is large enough to detain the volume of slurry received there in long enough to produce an acidified material and the size of said second chamber is large enough to detain the volume of slurry received therein from the first chamber long enough to generate methane gas which is collected in said fourth chamber.

2. A digester as defined in claim 1 including heating coils positioned about said second chamber for heating the slurry therein.

3. A digester as defined in claim 1 including a mix tank for preparing the slurry and having a connection to said input line, a recycle line having one end connected to the bottom of a flexible tube in said third chamber, and float means for supporting the upper end of said flexible tube adjacent the surface of the slurry in the third chamber, the other end of said recycle line connected to said mix tank.

4. The digester as defined in claim 1 including upper gas jets located on one side of the chambers and lower gas jets located on the opposite side of the chambers for circulating the slurry therein after the periodical feeding of a load of raw slurry into the bottom of the first chamber.

5. A digester as defined in claim 1 wherein said digester is formed of a flexible oblong bag having its lower half portion supported in a trench dug in the earth and a first and second divider, the lower half portion of the bag being separated by said first and second divider to form said first, second and third chambers, and the upper half portion of said bag forming said fourth chamber, and wherein said first passthrough tube is elbow shaped with its lower end extending through an opening in the bottom of said first divider and with its upper free end disposed on the central level portion of the first chamber, and wherein said second passthrough tube is straight and extends through an opening in the bottom of said second divider.

6. The digester as defined in claim 5 wherein said first divider has a weir formed on the upper end thereof.

7. The digester as defined in claim 5 including a gas outlet pipe flexibly connected to the upper half portion of said bag, said gas outlet pipe providing for feeding gas to a compressor.

8. The digester as defined in claim 5 including a compressor on-off control switch coupled to sense the expansion and contraction of the upper half portion of said bag.

9. The digester as defined in claim 5 wherein said bag and said first and second dividers are formed of a nylon reinforced synthetic rubber structural fabric.

10. A process for the producing of a methane gas and a liquid fertilizer from organic matter comprising the steps of:

blending a slurry of organic waste matter containing aerobic and anaerobic bacteria in a mix tank providing a first, second and third chamber interconnected in tandem by passthrough tubes such that the central level portion of the first chamber is connected to the bottom level portion of the second chamber and the bottom level portion of the second chamber is connected to the bottom level portion of the third chamber, the size of the second chamber being larger than the size of either the first or third chambers;

providing a flexible gas collecting chamber above and covering first, second and third chambers;

initially filling said first, second and third chambers with slurry from said mix tank to the level of an output port provided by the upper end of an upright pipe in the third chamber; and periodically feeding a predetermined volume of slurry less than the volume of the first chamber from the mix tank into the bottom of the first chamber and automatically creating a movement of a like volume of the slurry from said first chamber to said second chamber, from said second chamber to said third chamber; and from said third chamber into the outlet port;

wherein the size of said first chamber is large enough to detain the volume of slurry received therein from the mix tank long enough to react to aerobic bacteria and anaerobic bacteria to produce an acidified material and the size of said second chamber is large enough to detain the volume of slurry received therein from the first chamber long enough to further react to anaerobic bacteria to generate methane gas;

whereby the digested slurry received in the third chamber from the second chamber and drained down said outlet port corresponds to liquid fertilizer and permitting the slurry in the second chamber to remain long enough to generate methane gas which is collected in said fourth chamber.

11. The process of claim 10 including the step of agitating the slurry in said slurry chambers after the periodical feeding of the slurry from the mix tank into the first chamber.

* * * * *